United States Patent [19]

Moore

[11] 4,121,539

[45] Oct. 24, 1978

[54] ANIMAL ENCLOSURE SYSTEM WITH WASTE TREATMENT MEANS

[76] Inventor: Joseph Terrell Moore, Rte. #1, Dixie, Ga. 31629

[21] Appl. No.: 768,320

[22] Filed: Feb. 14, 1977

[51] Int. Cl.² .............................................. A01K 1/00
[52] U.S. Cl. ..................................................... 119/28
[58] Field of Search ...................... 119/28, 16; 210/55, 210/523, 525, 526

[56] References Cited

U.S. PATENT DOCUMENTS

| | | | |
|---|---|---|---|
| 2,604,443 | 7/1952 | Fipps | 210/525 X |
| 3,662,715 | 5/1972 | Schapler | 119/28 |
| 3,865,727 | 2/1975 | Broling et al. | 210/523 X |
| 3,918,404 | 11/1975 | Bunger | 119/28 |
| 4,008,689 | 2/1977 | Albers | 119/28 |

Primary Examiner—Hugh R. Chamblee

Attorney, Agent, or Firm—Beveridge, DeGrandi, Kline & Lunsford

[57] ABSTRACT

An animal-supporting platform receives solid waste excreted by the animals. A mixture of the waste and a carrier liquid are treated in airtight holding tanks where ammonia gas is produced at ambient temperatures. The material is then fed to an airtight chamber provided with liquid overflow means and a liquid outlet passage which leads downwardly from the overflow means and then upwardly to a discharge point located outside the chamber. Combustible methane gas generated by decomposition of the waste material is discharged through a gas outlet opening located in an upper portion of the chamber, and undigested solids are moved through the chamber and then removed from the chamber by a conveyor means leading through a submerged chamber outlet opening.

13 Claims, 4 Drawing Figures

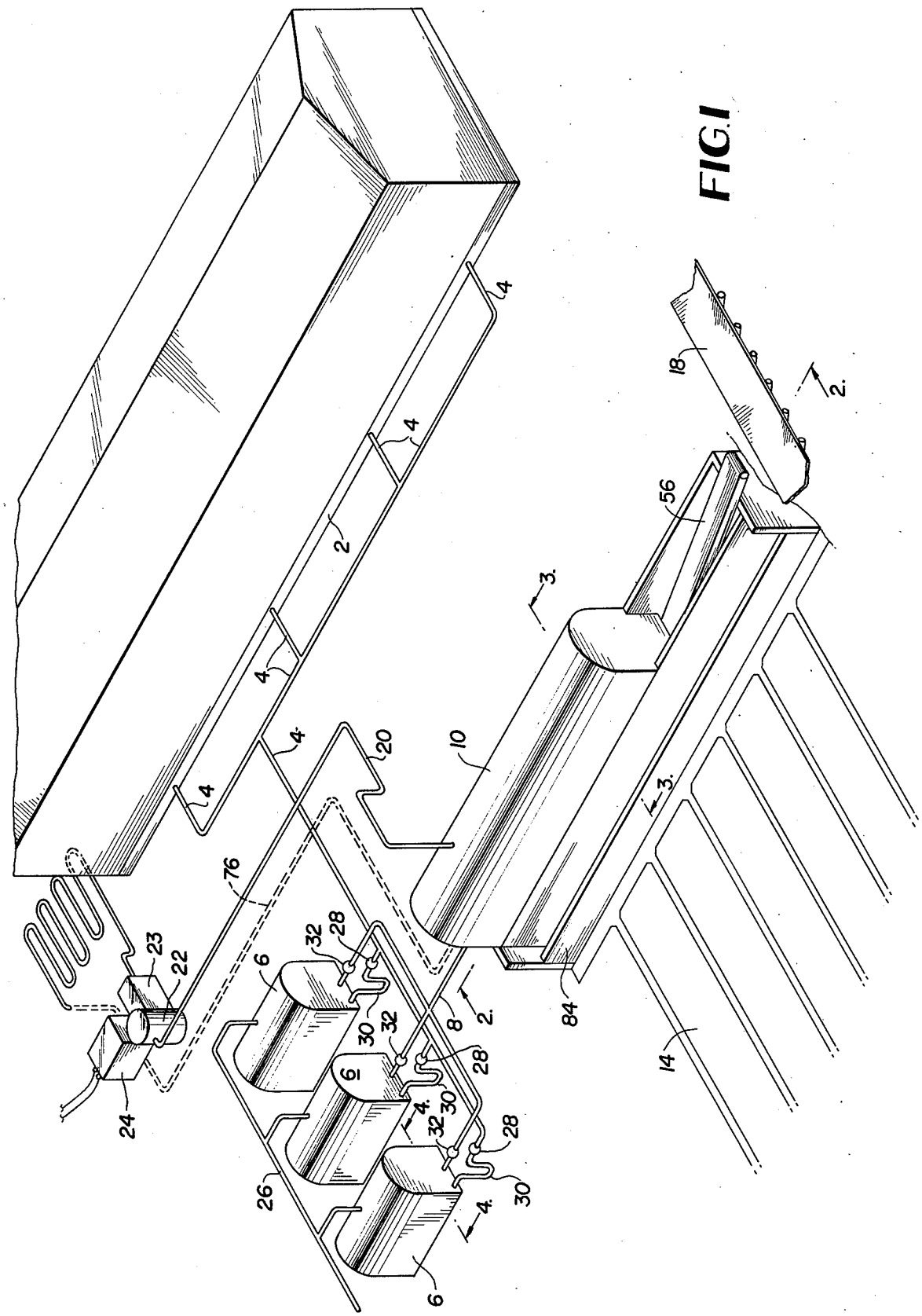

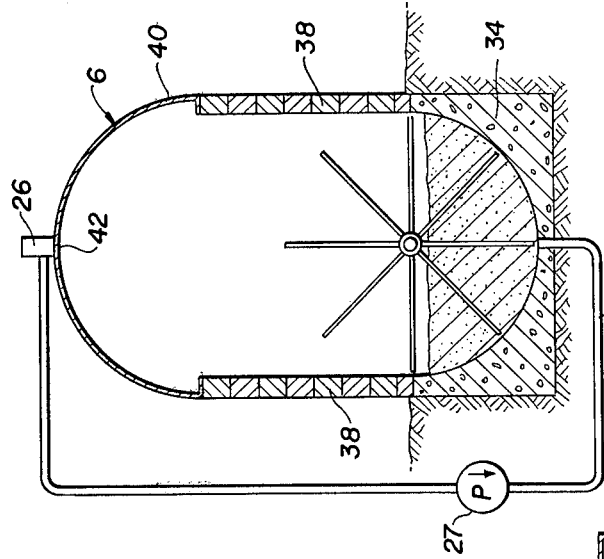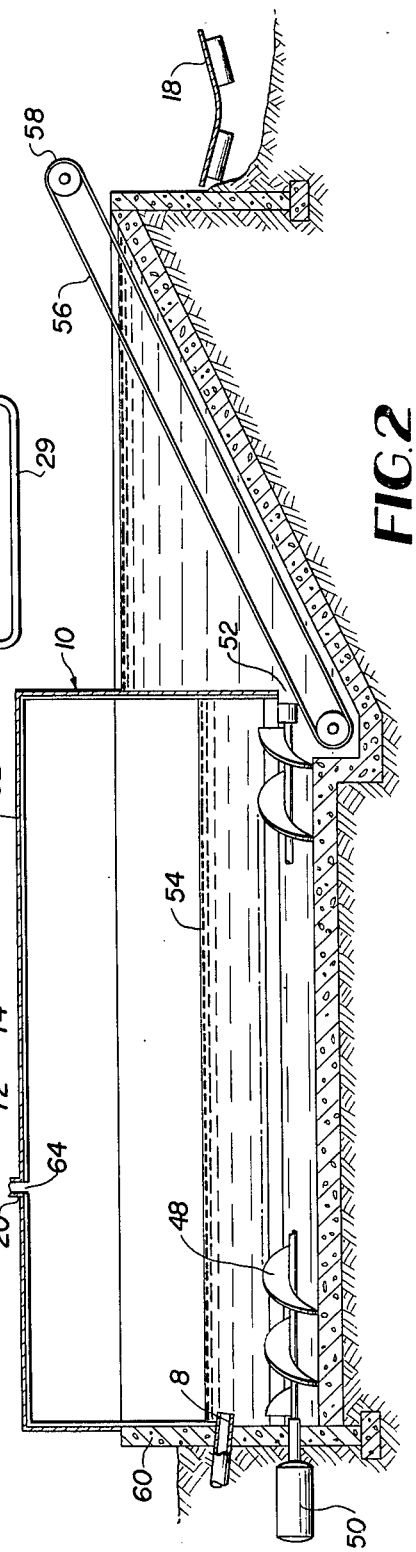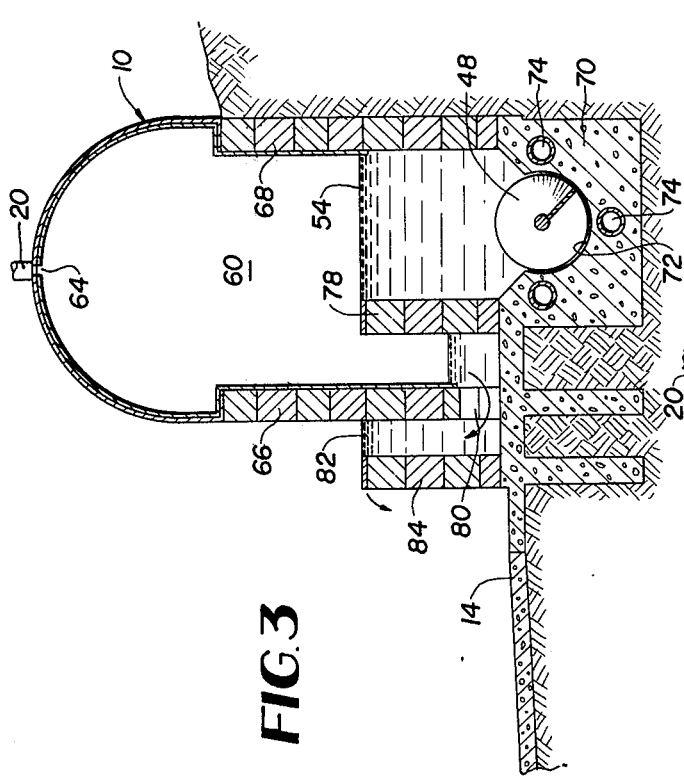

4,121,539

ANIMAL ENCLOSURE SYSTEM WITH WASTE TREATMENT MEANS

BACKGROUND AND SUMMARY OF THE INVENTION

This invention relates to the field of animal husbandry and particularly to a system for receiving waste material excreted by the animals, bacterially decomposing the material to produce methane gas, and separating and removing the liquid and solid products of such bacterial decomposition.

It is widely known that a product of bacterial decomposition of sewage and animal waste is methane gas. Many proposals have been made for collecting and utilizing such gas in municipal sewage systems and in conjunction with animal feed lots, dairy barns and other animal enclosures. None of these proposals has met with a significant degree of success. Although the specific reasons for prior failures are not known to the present inventor, it is believed that one of the primary problems has related to the presence of excessive liquid content and difficulties or inabilities in removing liquids and solids from chambers where the waste materials are undergoing treatment.

It is an object of this invention to provide an uncomplicated but efficient system for raising animals and handling the waste materials excreted thereby to produce methane gas.

Another object of the invention is to provide an animal enclosure system with a methane gas generator which has a satisfactory means for removing excess liquid from the material undergoing treatment, and/or for removing undigested dense solids from the chamber where the material is being treated.

A further object is to provide for pretreatment of the animal waste material in a holding tank system which permits process controls and produces ammonia gas.

Another object is to provide a complete system which utilizes available solar energy and vegetation nutrient by-products from the system.

Still another object to process animal waste material under conditions which optimize gas generation and conserve to a maximum extent all materials produced by the system.

According to one basic principle of the invention, an animal enclosure system has a platform for supporting animals and receiving their solid wastes, a gas enclosing digestion chamber for containing a mixture of the animal waste and water or other carrier liquid, means for conducting waste from the platform to the chamber, a gas outlet opening located in an upper portion of the chamber above the mixture, a conveyor for moving dense solids through the bottom of the chamber from the inlet end to the solids outlet opening, and then to a discharge point outside the chamber and above the liquid level. Liquid from within the chamber passes over an overflow means which maintains the mixture at a given liquid level. A liquid outlet passage leads downwardly from the overflow point and then upwardly to a discharge point located outside the chamber. Liquid discharged from the treatment chamber may go to an evaporation lagoon.

A plurality of holding tanks are provided for receiving the waste material from the animal platform and holding the waste material at ambient atmospheric temperatures to permit the bacterial generation of ammonia gases prior to delivery of the waste materials to the methane generation chamber which preferably is heated to promote the methane-generating bacterial activity.

Other inventive concepts are within the purview of the invention, only a typical example of which is described hereinbelow.

BRIEF DESCRIPTION OF THE DRAWINGS

FIG. 1 is a perspective view of a complete facility constructed according to the invention;

FIG. 2 is a longitudinal section view through the methane generating chamber and the solids-handling system associated therewith;

FIG. 3 is a transverse sectional view through the apparatus of FIG. 2; and,

FIG. 4 is a vertical section taken through one of the holding tanks.

BRIEF DESCRIPTION OF A PREFERRED EMBODIMENT

The overall layout of a preferred system for practicing the invention is shown in FIG. 1 which illustrates in diagramatic form an animal platform 2 for supporting livestock or dairy animals and receiving the solid waste excreted by the animals. The solid waste may be removed by mechanical or fluid cleansing systems, an example of the latter being disclosed in U.S. Pat. No. 3,223,070 issued Dec. 14, 1965, to Gripple and Bennett which is incorporated herein by reference.

Waste from the animal platform 2 is carried by a network of pipes 4 to any one of a series of holding tanks 6, details of which are described in a later portion of this specification. From the holding tanks 6, the waste material passes through an infeed pipe 8 to the main digestion chamber 10 where the waste material and a carrier liquid are digested by bacterial action to break down the solids and to generate methane gas. The material is separated into liquid and nondigestible solids, the liquid being discharged over the wall 84 into an evaporation lagoon 14 which receives the liquids from the liquid outlet passage of the chamber 10 and supports the liquid for evaporation. Undigestible solids are carried from chamber 10 by a conveyor 16 to a drying belt 18 where they are exposed to the sun and atmosphere for drying.

In the course of digestion, methane gases are generated in chamber 10. These gases pass through a gas outlet opening in the upper portion of the chamber 10 above the liquid level therein and are carried by a gas pipe 20 to a gas storage or utilization facility. In the illustrated embodiment, the gas conduit 20 leads to a gas tank 22. A boiler 23 is fired by gas from tank 22 to generate steam for driving a turbine in the electric generator 24.

The holding tanks 6 are located in the flow path between the animal platform 2 and the main digestion chamber 10 of the apparatus. These airtight holding tanks 6 permit control of the infeed to the chamber 10 and provide for a preliminary digestion of the animal waste, this preliminary digestion preferably being conducted at ambient temperatures at which ammonia-generating bacteria will act on the waste material to break it down and create ammonia gas which is removed from the holding tanks 6 by a conduit system 26 illustrated in FIG. 1.

The holding tank 6 are connected to the piping system 4 by manually operable valves which lead to the holding tank inlet conduits which include the U-traps 30 which keep unwanted air out of the respective holding tanks. When a holding tank 6 is filled to the desired depth such as that illustrated in FIG. 4, the tank's inlet valve 28 is closed and the ammonia-generating bacteria are permitted to operate on the tank contents, preferably during agitation which will be described later in connection with FIG. 4. Ultimately, the tank contents are fed to the main treatment chamber 10 by opening the associated valve 32 in the holding tank outlet conduit, releasing the holding tank contents to the infeed pipe 8 for main chamber 10.

A cross sectional view of the holding tank is shown in FIG. 4 where it will be seen that it comprises a cast concrete foundation 34 of arcuate interior configuration, the upper edges of the foundation 34 providing footings for masonry walls 36 and 38. The interior surfaces of the foundation 34 and walls 36 and 38 are coated with an airtight noncorrosive solution. A hood 40 is attached and sealed to the upper surfaces of the walls 38 and is provided with a gas outlet opening at 42 which leads to the conduit system 26 which receives gaseous ammonia from within the holding tank. The airtight integrity of the tank 6 may be assured by providing it with a continuous plastic liner which extends upwardly from below the liquid level. Alternatively, the tanks 6 and 10 may be formed of fiber reinforced plastic such as Fiberglas rather than of masonry materials.

It is known that the ammonia-generating bacterial activity in a body of waterborne solid animal waste is enhanced by agitation which disturbs and breaks up the upper surface of the material. Toward this end, the apparatus shown in FIG. 4 includes a shaft 44 which carries a paddle wheel with blades 46. A motor rotates the shaft, causing the blade 46 to agitate constantly the material within the holding tank 6. In lieu of or in addition to the paddle wheel, the tank 4 may be provided with a gas recirculation pump 27 which, via line 29, introduces gas into a submerged area of the tank chamber to agitate the chamber contents.

Although not shown, each holding tank may have a tap located at the desired liquid level for removing excess water, and a submerged air injection nozzle for adding air to the tank contents. As previously mentioned, the main treatment chamber 10 functions to permit digestion of a mixture of the animal waste material and liquid. This breaks down the solid material and generates methane gas. The construction of chamber 10 also enables the removal of excess liquid from the material and the conveyance from the chamber of non-digestible solids.

Details of construction of the chamber 10 may be seen in FIGS. 2 and 3. Waste material, in the form of a slurry from the holding tanks, is received in the chamber 10 through the infeed pipe 8 located at the left or inlet end of the chamber 10 as shown in FIG. 2. An auger or feed screw conveyor 48 driven slowly by a motor 50 with appropriate reduction gearing extends longitudinally of the chamber 10 to carry more dense non-digestible solid materials to the solids outlet opening 52 at the right or outlet end of the chamber, below the liquid level 54. The auger rotates at a speed which carries materials from the infeed end to the outfeed end of the chamber in about 10-15 days. These dense undigestible solids are then carried by an inclined belt conveyor 16 upwardly from the solids outlet opening 52 to a discharge point 58 which is above the liquid level 54. From discharge point 58, the solids fall on the drying belt conveyor 18 which was described in connection with FIG. 1.

The chamber 10 includes an end wall 60 and a hood 62 which entraps the methane gases produced by the digestive action and releases them through the gas outlet opening 64 to the gas pipe 20. The hood extends downwardly below the liquid level 54 to form the outlet end of the chamber 10. Of course, the gas outlet opening 64 must be in an upper portion of the chamber 10 above the liquid level 54. Gas passing through the outlet opening 64 may be handled by well known methods and devices. A pressure regulator or relief valve may operate to maintain a constant gas pressure in the tank. Pumps, purifiers, compressors and the like may be installed as needed or desired.

The transverse sectional view of FIG. 3 illustrates the structure for removal of liquid from the material undergoing processing in chamber 10. The sides of the chamber 10 are formed by masonry side walls 66 and 68, upon which the hood 62 is supported. A concrete foundation 70 supports the side walls 66 and 68 and forms the bottom of the chamber 10. The foundation is arcuately recessed at 72 to receive the auger conveyor 48. Heating pipes 74 are located in the foundation adjacent to the recess 72. A heating medium is circulated through the pipes 74 to heat the liquid undergoing treatment in the chamber 10 to a temperature of about 90° to 115° F. to promote the bacterial action which decomposes the solid waste materials and generate methane gas. The heating medium may be steam or condensed hot water carried to the pipes 74 by pipe 76 from the generator 24 as shown in FIG. 1.

Airtightness of chamber 10 is quite important so it is desirable to coat the interior masonry and concrete surfaces with an airtight noncorrosive solution, and to provide an airtight plastic liner for the chamber 10, especially in those areas above the liquid level and extending to a level below the liquid surface.

In order to maintain the liquid level 54 at a constant elevation within the tank 10, and to permit withdrawal of liquid from the tank, there is a longitudinal interior wall 78 which extends the full length of chamber 10 so that its upper edge provides an overflow weir communicating with the chamber 10. The side wall 66 is provided with lower liquid releasing openings 80 to permit the liquid in the space between walls 66 and 78 to seep through wall 66 and enter a space 82 located outside the chamber 10. The chamber 82 is formed on one side by the side wall 66 of chamber 10 and other the other side by the exterior wall 84 which is located outside the chamber and lies substantially parallel to the interior wall 78. Preferably, the upper edge of the exterior wall 84 is at the same elevation as the upper edge of the interior overflow wall 78. The existence of a pressure in the chamber 10 greater than atmospheric pressure will cause the liquid level in the interior space between walls 66 and 78 to lie below the liquid level in the exterior space 82. Water passing through the openings 80 will cause liquid in space 82 to overflow the wall 84, discharging the liquid into the evaporation lagoon 14 where it will be exposed to the atmosphere for evaporation. Hydroponic crops may be grown in the lagoon, as there are plant nutrients in the liquid effluent from the system.

From the preceding description of the structure and operation of the walls 78, 66 and 84, it will be realized that they form with the openings 80 a liquid outlet passage which leads downwardly from an overflow point in the chamber and then upwardly to a discharge point located outside the chamber 10.

The operation of the disclosed system will readily be understood. The animal waste accumulating on the platform 2 will periodically be flushed or otherwise removed and carried to the holding tanks 6. This is preferably done on a daily basis so that bacterial action may commence less than 24 hours after excretion. The waste and flushing water from platform 2 are carried through the network of pipes 4 to one of the holding tanks 6. This is done by opening the inlet valve 28 in the holding tank and permitting the holding tank to fill to the level shown in FIG. 4 through the tank inlet conduit which includes the trap 30. The capacity of each holding tank 6 is selected to enable it to receive one day's washings from the platform. The valve 28 is closed when the material achieves the desired depth in the holding tank 6. The agitator paddles 46 are continuously rotated while the holding tank remains at ambient atmospheric temperatures preferably below about 80° F. so that bacterial action will occur in the material to achieve some decomposition and to generate ammonia gas which is removed from the holding tanks through the ammonia conduit system 26. The ammonia gas may be processed into fertilizer or to other well known materials.

After being processed about two or three days in a holding tank, the partially decomposed mixture of animal waste and water is directed to the main chamber 10 by opening the outlet valve 32 on a holding tank 6 to release the holding tank contents to the infeed pipe 8 of chamber 10. The material enters the inlet end of chamber 10 and progresses longitudinally at a very low rate from the inlet end to the outlet end of the chamber 10. While in the chamber 10, bacterial action decomposes much of the solids and generates methane gas which is trapped by the hood 62 and discharged through gas outlet opening 64 to the methane system pipe 20. Those solids which are not digested are advanced by the auger conveyor 48 to the solids outlet opening 52 of the chamber 10, where it falls on the belt conveyor 16 which moves the undigested solids upwardly from the solids outlet opening to a discharge point outside the chamber 10 and above the liquid level 54.

Within the chamber 10, there is some gravitational separation causing the surface at liquid level 54 to be primarily liquid. The liquid is removed from chamber 10 by first passing over the longitudinal overflow walls 78 and through the liquid releasing openings 80 in the side wall 66 of the chamber. Any floating solids entering the space between walls 78 and 66 cannot leave the chamber, but may be removed manually during shutdown periods. The water, entirely free of solids, then ascends through the space 82 to a point where it will flow over the upper edge of the exterior wall 84 into the evaporation lagoon 14. The evaporation lagoon 14 supports the liquid and permits it to evaporate under normal atmospheric conditions. Algae growing in the lagoon may be harvested and prepared for animal feed, or may be fed into the main digestion chamber 10 for decomposition.

The solids removed from the chamber 10, after being carried upwardly by the belt conveyor 16, fall onto a drying conveyor 18 where it is dried either by conventional drying heaters or by exposure to solar radiation. It may then be mixed with soil as is conventional with sewage sludge.

The methane gas generated by the apparatus may be used in many different ways. It may be used in its original form which includes many impurities or it may be purified before use. According to the preferred embodiment, the methane is used to fire burners in the boiler 23, generating steam which drives a turbine in the electrical generator 24.

It is emphasized that this specification has disclosed only a preferred embodiment of a system constructed according to the invention. Many changes may be made thereto without departing from the inventive spirit, so it should be kept in mind that the invention is not limited only to the disclosed embodiment but encompasses modifications and variations thereof which fall within the spirit of the claims which follow.

I claim:
1. An animal enclosure system, comprising,
a platform for supporting animals and for receiving solid waste excreted by said animals,
a gas enclosing chamber means for containing in a lower portion thereof a mixture of said waste and a carrier liquid,
means for conducting waste from said platform to said chamber means,
a gas outlet opening located in an upper portion of said chamber means above said mixture,
said chamber means having an inlet end and an outlet end,
overflow means in communication with said chamber means for maintaining the mixture undergoing treatment in the chamber means at a given liquid level,
a liquid outlet passage leading downwardly from the overflow means and then upwardly to a discharge point located outside said chamber means,
a solids outlet opening located at the outlet end of the chamber means below the liquid level,
conveyor means for moving solids through the bottom of the chamber from said inlet end to said solids outlet opening and then upwardly from the solids outlet opening to a discharge point outside the chamber means and above the liquid level.
2. The apparatus of claim 1 having an evaporation lagoon means receiving liquid from the liquid outlet passage and supporting such liquid for evaporation.
3. The apparatus of claim 1 having means for heating the mixture in said chamber means.
4. The apparatus of claim 1 having means for generating electrical power, and boiler means connected to and fired by gas from said chamber means for operating said generating means.
5. The apparatus of claim 1 wherein the overflow means is a longitudinal interior wall within the chamber means, an exterior wall located outside said chamber means and extending substantially parallel to said interior wall, and lower liquid releasing openings in said chamber means between said interior and exterior walls at an elevation below the upper edges of said interior and exterior walls, said liquid outlet passage being formed by said liquid releasing openings and said interior and exterior walls.
6. The apparatus of claim 5 having an evaporation lagoon means receiving liquid from the liquid outlet passage and supporting such liquid for evaporation.
7. The apparatus of claim 5 having means for heating the mixture in said chamber means.
8. The apparatus of claim 5 wherein the means for conducting waste from said platform to said chamber means includes a plurality of holding tanks, each holding tank having an inlet conduit connected to and receiving solid waste material from said animal platform, each holding tank having an outlet conduit connected to and discharging said waste material to said chamber means.

9. The apparatus of claim 8 wherein each holding tank has an agitator means for stirring the contents of each said holding tank, a gas outlet opening located in an upper portion of each said holding tank, valve means in said inlet conduit to permit filling of each said holding tank, and valve means in said outlet conduit for releasing the contents of each said holding tank to said chamber means.

10. The apparatus of claim 1 wherein the means for conducting waste from said platform to said chamber means includes a plurality of holding tanks, each holding tank having an inlet conduit connected to and receiving solid waste material from said animal platform, each holding tank having an outlet connected to and discharging said waste material to said chamber means.

11. The apparatus of claim 10 wherein each holding tank has an agitator means for stirring the contents of each said holding tank, a gas outlet opening located in an upper portion of each said holding tank, valve means in said inlet conduit to permit filling of each said holding tank, and valve means in said outlet conduit for releasing the contents of each said holding tank to said chamber means.

12. The apparatus of claim 10 having an evaporation lagoon means receiving liquid from the liquid outlet passage and supporting such liquid for evaporation.

13. The apparatus of claim 10 having means for heating the mixture in said chamber means.

* * * * *